US010576516B2

(12) United States Patent
Daneu (10) Patent No.: US 10,576,516 B2
(45) Date of Patent: Mar. 3, 2020

(54) PROCESS FOR TREATING SOLID WASTE CONTAINING AN ORGANIC FRACTION

(71) Applicant: AGATOS GREEN POWER LEMURIA S.R.L., Milan (IT)

(72) Inventor: Alessandro Daneu, Rodange (LU)

(73) Assignee: AGATOS GREEN POWER LEMURIA S.R.L., Milan (IT)

(*) Notice: Subject to any disclaimer, the term of this patent is extended or adjusted under 35 U.S.C. 154(b) by 159 days.

(21) Appl. No.: 15/570,626

(22) PCT Filed: Apr. 28, 2016

(86) PCT No.: PCT/IB2016/052414
§ 371 (c)(1),
(2) Date: Oct. 30, 2017

(87) PCT Pub. No.: WO2016/174609
PCT Pub. Date: Nov. 3, 2016

(65) Prior Publication Data
US 2018/0354007 A1    Dec. 13, 2018

(30) Foreign Application Priority Data

Apr. 29, 2015    (IT) .................. 102015000013526

(51) Int. Cl.
*B09B 3/00*    (2006.01)
*A61L 2/04*    (2006.01)
(Continued)

(52) U.S. Cl.
CPC .............. *B09B 3/0083* (2013.01); *A61L 2/04* (2013.01); *A61L 12/00* (2013.01);
(Continued)

(58) Field of Classification Search
CPC ..... C02F 11/04; C02F 11/185; C02F 2209/02; C02F 3/006; C02F 3/28; C02F 3/286;
(Continued)

(56) References Cited

U.S. PATENT DOCUMENTS

| | | | | |
|---|---|---|---|---|
| 2005/0028680 | A1* | 2/2005 | Thompson | C02F 11/185 99/455 |
| 2012/0125840 | A1* | 5/2012 | Smith | C12M 41/48 210/631 |
| 2014/0349360 | A1* | 11/2014 | Zhang | C10L 1/02 435/162 |

FOREIGN PATENT DOCUMENTS

| | | |
|---|---|---|
| CN | 1130355 A | 9/1996 |
| CN | 101786771 A | 7/2010 |

(Continued)

OTHER PUBLICATIONS

International Search Report for PCT/IB2016/052414, ISA/EP, Rijswijk, NL, dated Jul. 28, 2016.
(Continued)

*Primary Examiner* — Claire A Norris
(74) *Attorney, Agent, or Firm* — Harness, Dickey & Pierce, P.L.C.

(57) ABSTRACT

Process for treating solid waste containing an organic fraction, comprising an initial step of extrusion pressing the waste with production of a solid fraction and a liquor. The solid fraction is subjected to a milling treatment at a pressure lower than the atmospheric pressure in a rotary mill that produces a sanitized dry solid and water. The liquor is subjected to a treatment of anaerobic digestion in three subsequent steps, with production of biogas and of a digestate that is subjected to evaporation under vacuum to obtain a concentrated compost and steam, re-used in other steps of the process. The sanitized dry solid and the biogas can be used as fuel to produce thermal and electric energy to be (Continued)

used in the process, which also allows surplus energy to be obtained.

7 Claims, 4 Drawing Sheets

(51) Int. Cl.
| | | |
|---|---|---|
| C02F 1/04 | (2006.01) | |
| C02F 3/28 | (2006.01) | |
| C05F 9/02 | (2006.01) | |
| C05F 9/04 | (2006.01) | |
| B09B 5/00 | (2006.01) | |
| B02C 18/00 | (2006.01) | |
| A61L 12/00 | (2006.01) | |
| B02C 18/12 | (2006.01) | |
| B30B 9/02 | (2006.01) | |
| C10L 3/00 | (2006.01) | |
| C10L 5/46 | (2006.01) | |

(52) U.S. Cl.
CPC .......... *B02C 18/0084* (2013.01); *B02C 18/12* (2013.01); *B09B 3/00* (2013.01); *B09B 5/00* (2013.01); *B30B 9/02* (2013.01); *C02F 1/048* (2013.01); *C02F 3/286* (2013.01); *C02F 3/2893* (2013.01); *C05F 9/02* (2013.01); *C05F 9/04* (2013.01); *C10L 3/00* (2013.01); *C10L 5/46* (2013.01); *C02F 2203/006* (2013.01); *C02F 2301/106* (2013.01); *Y02E 50/343* (2013.01); *Y02W 30/43* (2015.05); *Y02W 30/47* (2015.05)

(58) Field of Classification Search
CPC .... C05F 17/0027; C05F 7/00; C05F 17/0018; C05F 17/0063; B09B 3/0083; B09B 3/00; B02C 18/0084
USPC .................................................. 210/605, 631
See application file for complete search history.

(56) References Cited

FOREIGN PATENT DOCUMENTS

| | | |
|---|---|---|
| CN | 102321673 A | 1/2012 |
| DE | 19833776 A1 | 2/2000 |
| JP | S5644086 A | 4/1981 |
| JP | S58-150497 A | 9/1983 |
| JP | H07-284749 A | 10/1995 |

OTHER PUBLICATIONS

Written Opinion of the ISA for PCT/IB2016/052414, ISA/EP, Rijswijk, NL, dated Jul. 28, 2016.

* cited by examiner

PROCESS FOR TREATING SOLID WASTE CONTAINING AN ORGANIC FRACTION

CROSS-REFERENCE TO RELATED APPLICATIONS

This application is a 371 U.S. National Stage of International Application No. PCT/IB2016/052414, filed Apr. 28, 2016, which claims the benefit of and priority to Italian Patent Application No. 102015000013526, filed Apr. 29, 2015. The disclosures of the above applications are incorporated herein by reference.

The present invention relates to a process for treating and exploiting solid waste containing an organic fraction, coming both from separate and unsorted waste collection, and to a plant used to carry out this process.

In Italian legislation the initials RSU designate urban solid waste coming from unsorted municipal waste collection (MSW, Municipal Solid Waste), and the initials FORSU designate the organic fraction of the waste obtained from separate collection.

There are many known processes for treating solid waste, based both on combustion, or waste-to-energy, and on conversion of the waste to obtain recyclable fractions that can be re-used in various applications, including combustion, or an end product suitable to be disposed of in legally operated landfills.

Some of the known processes are not cost-effective, either because they consume large amounts of energy or because they do not allow complete recycling of the components of the waste received, whether this is FORSU or RSU, still causing problems linked to pollution, or for both these reasons.

The most advanced treatment processes use a combined mechanical and biological treatment (MBT). Mechanical treatment essentially consists of pressing, with which a solid fraction is separated from a liquid or semi-liquid fraction destined for biological stabilization treatment. With subsequent refining steps, a fuel from waste (FFW) can be obtained.

However, these known processes do not allow maximum recovery, and consequently exploitation, of the waste up to levels close to 100%. In fact, they produce, albeit to a limited extent, further process waste.

Therefore, it would be desirable to provide a process capable of maximizing waste recovery without producing further waste and pollution, transforming it into fractions and/or products that can be used further, and which therefore have a market value, such as fuels, substantially clean water and nitrogen compounds for use in agriculture.

Therefore, an aspect of the invention relates to a process for treating solid waste containing an organic fraction, comprising an initial step of extrusion pressing the waste with production of a solid fraction and a liquor, characterized in that:
a) said solid fraction is subjected to a milling treatment at a pressure lower than the atmospheric pressure in a rotary mill that causes said solid fraction to heat from a room temperature to a sanitization temperature of from 55 to 160° C., said temperature being adjusted by controlled evaporation of water present in or introduced into said solid fraction, said milling treatment at a pressure lower than the atmospheric pressure producing a sanitized dry solid and water;
b) said liquor is combined to said water produced in said milling treatment of said step a) and is subjected to a treatment of anaerobic digestion in three subsequent steps, comprising a first step of mesophilic fermentation at a temperature from 35 to 45° C., a second step at a temperature from 65 to 90° C., in which a pasteurization treatment is carried out, and a third step of thermophilic fermentation at a temperature from 50 to 60° C., said treatment of anaerobic digestion producing biogas and a digestate comprising a solid component dispersed in water;
c) said digestate is subjected to an evaporation treatment of said water under vacuum in one or more steps, thereby producing a concentrated compost and steam which is condensed with formation of water which is in part used in other steps of the process and in part made available to be reused in the civil or agricultural or industrial field;
wherein said sanitized dry solid produced in said step a) and said biogas produced in said step b) are suitable to be used as fuel to produce thermal and electric energy to be used in said process, and said compost produced in said step c) is suitable to be used as fertilizer or improver in agriculture or added to said solid fraction in said step a).

Another aspect of the invention relates to a plant which can advantageously be used to carry out the process for treating solid waste defined above.

This plant comprises an extrusion press for waste to produce a solid fraction and a liquor, a rotary mill to mill and heat said solid fraction, and a digestor for the anaerobic fermentation of said liquor, characterized in that said digestor comprises three concentric tanks consisting of an external tank for the treatment of mesophilic fermentation, an internal tank for the pasteurization treatment, and an intermediate tank for the treatment of thermophilic fermentation. According to another aspect of the invention, the plant is characterized in that said internal tank consists of three separate chambers, comprising:
a) a first inlet chamber in which the liquid coming from the mesophilic step is distributed;
b) a second intermediate chamber of thermal exchange, which is not in communication with said first chamber;
c) a third chamber, of pasteurization, which is in communication with said first chamber and said second chamber, and which is adapted to receive the liquid coming from said first chamber through a series of pipes that extend into said second chamber hydraulically sealed from said second chamber, and to discharge said liquid in said second chamber through an exit pipe, said pasteurization chamber being equipped with a heating jacket;
wherein said second chamber is equipped with a line to discharge the liquid from said internal tank into said intermediate tank for thermophilic fermentation.

Some terms of the present description have the meaning defined below:

The term "solid fraction" designates the solid part of waste obtained in the initial step of extrusion pressing.

The term "liquor" designates the liquid or semi-liquid part of waste obtained in the initial step of extrusion pressing.

The term "sanitization temperature" designates a temperature of from 55 to 160° C., capable of destroying or inactivating the majority of microorganisms such as bacteria, fungi and spores. When the temperature exceeds 150° C. sterilization of the material treated is obtained. In the present description, sanitization temperature therefore also comprises the sterilization temperature.

The term "sanitized substance" designates the solid or liquid material that is subjected to sanitization treatment and is therefore bio-stabilized, i.e. it is no longer adapted to rot or be subject phenomena of putrefaction, with almost no risk of contamination.

The term "sterilization temperature" designates a process temperature exceeding 150° C., capable of destroying practically all microorganisms such as bacteria, fungi and spores.

The term "sanitized dry solid" designates the solid subjected to the sterilization treatment, therefore classified as inert.

The term "pasteurization treatment" designates a thermal decontamination process at a temperature from 65 to 75° C., adapted to destroy or inactivate many heat-sensitive potentially pathogenic microorganisms, such as bacteria in vegetative form, fungi and yeasts.

The term "compost" designates a soil deriving from the decomposition and humification of a mixture of organic matters that has been subjected to a sanitization process.

The term "rotary mill that causes said solid fraction to heat" is intended as a mill as described in the international patent application WO 95/003072.

A preferred embodiment of the invention, provided by way of non limiting example, will now be described with reference to the accompanying drawings, wherein.

Figure 1:
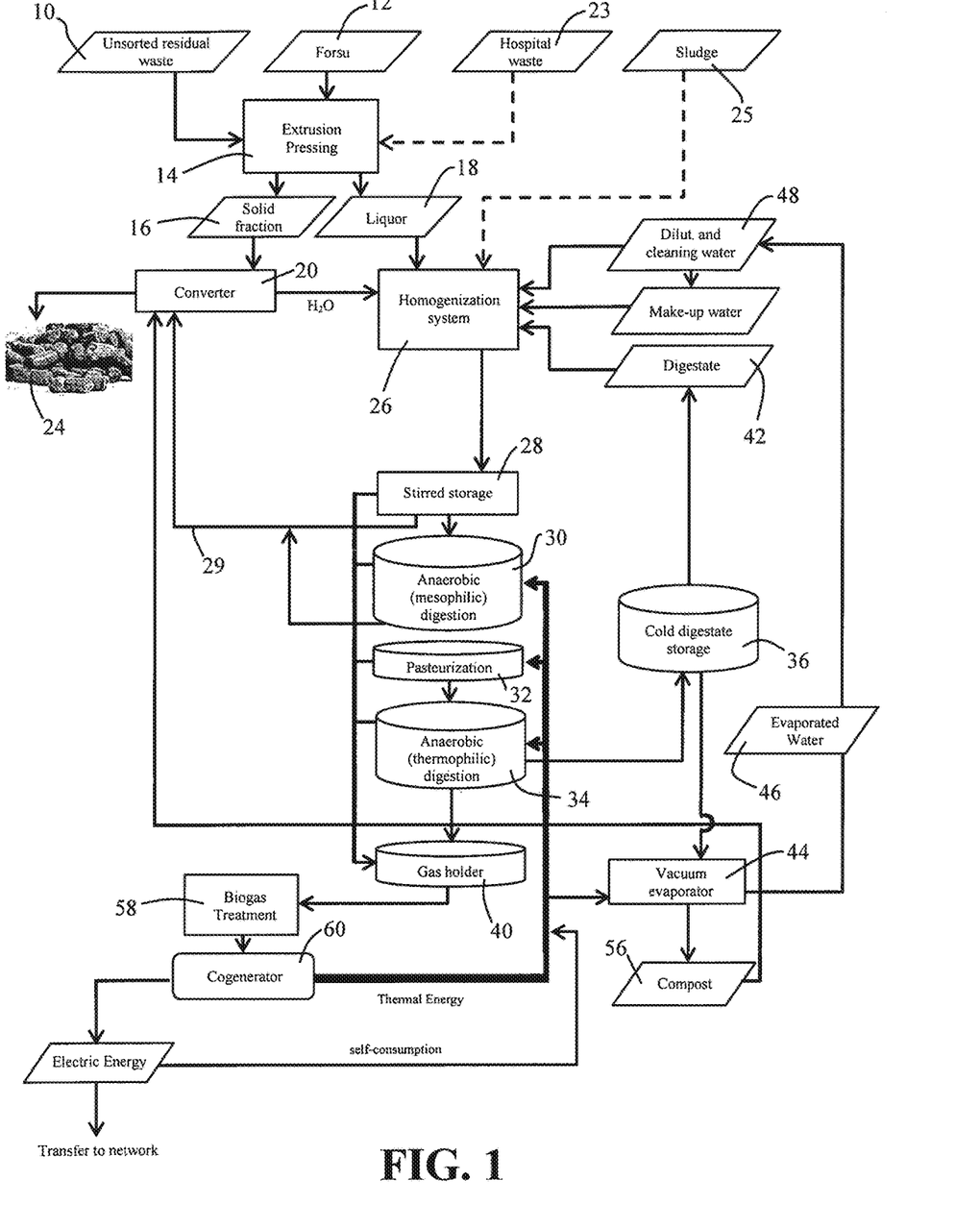
FIG. 1 is a block diagram of the steps of the process according to the invention.

With reference to FIG. 1, the process for treating solid waste according to the invention comprises a preliminary treatment for separating the inorganic substances present in the unsorted waste 10 (RSU), such as glass and stones, from the organic fraction. This latter, optionally combined with the organic fraction 12 (FORSU) coming from the separate collection, is sent to an initial step of extrusion pressing 14 carried out at high pressure, preferably from 20 to 100 MPa. This pressing of the waste produces a solid fraction 16 and a liquid or semi-liquid fraction 18. The solid fraction 16, which still contains residual moisture, usually forms 10-20% by weight in the case of treatment of the FORSU, and 20-50% in the case of treatment of the RSU, of the waste fed to the press.

The extrusion press comprises a watertight and sealed stainless steel hopper, inside which is a doser-vibrator for rapid feed of the waste to the pressing step.

With the extrusion pressing treatment the product is separated into two fractions: a solid fraction and a liquid or semi-liquid fraction, called liquor. The operating principle is based on physical separation of the two fractions and not on size-based separation.

By subjecting the waste to high pressure (operating pressure: of over 280 bar) in a perforated extrusion chamber, this causes fluidization of the actual organic parts (food residues, various putrescible fractions, etc.) that, driven by the difference in pressure inside and outside the chamber, are separated from the parts with greater mechanical strength, such as paper, cardboard, plastic, rubber, etc.

The extrusion press has a modular structure. The active part, the cylinders, the crank drives and all the functional members are positioned in a solid load-bearing structure made of electrowelded metal. The perforated extrusion chamber is located in the central part of the structure.

The extrusion-pressing cycle consists of three distinct and subsequent steps:

the feed step, during which the main cylinder transfers the material from the loading hopper into the extrusion chamber;

the extrusion step, during which the main cylinder carries out the actual compression, resulting in discharge of the wet organic fraction through the holes on the outer surface of the extrusion chamber;

the ejection step, during which the main cylinder ejects the dry fraction.

Operation of the machine is controlled by a hydraulic control unit. During processing, the liquid or semi-liquid fraction (liquor) is collected and conveyed underneath the machine towards the outside. The solid fraction is ejected towards the outside of the same machine through a specific opening on the top of the rear side of the machine.

According to an optional embodiment of the process according to the invention, it is also possible to treat hospital waste 23, which is fed to the milling step 14. In this case the rotary mill described below and called "converter" comprises a complete sterilization cycle also of the liquid part.

The solid fraction 16 is then subjected to a milling treatment 20 in a rotary mill that grinds the solid to reduce its size. A mill of this kind is described in general terms in the international patent application WO 95/003072, and is known in the art with the term "converter". However, according to the invention this mill has been modified to operate under vacuum at a pressure below 0.08 MPa, more preferably to operate at a pressure from 0.03 to 0.08 MPa. In these conditions, the water evaporates at a temperature around 70° C. so that the organic structure of the components usable in the digestor remains active.

Figure 2:
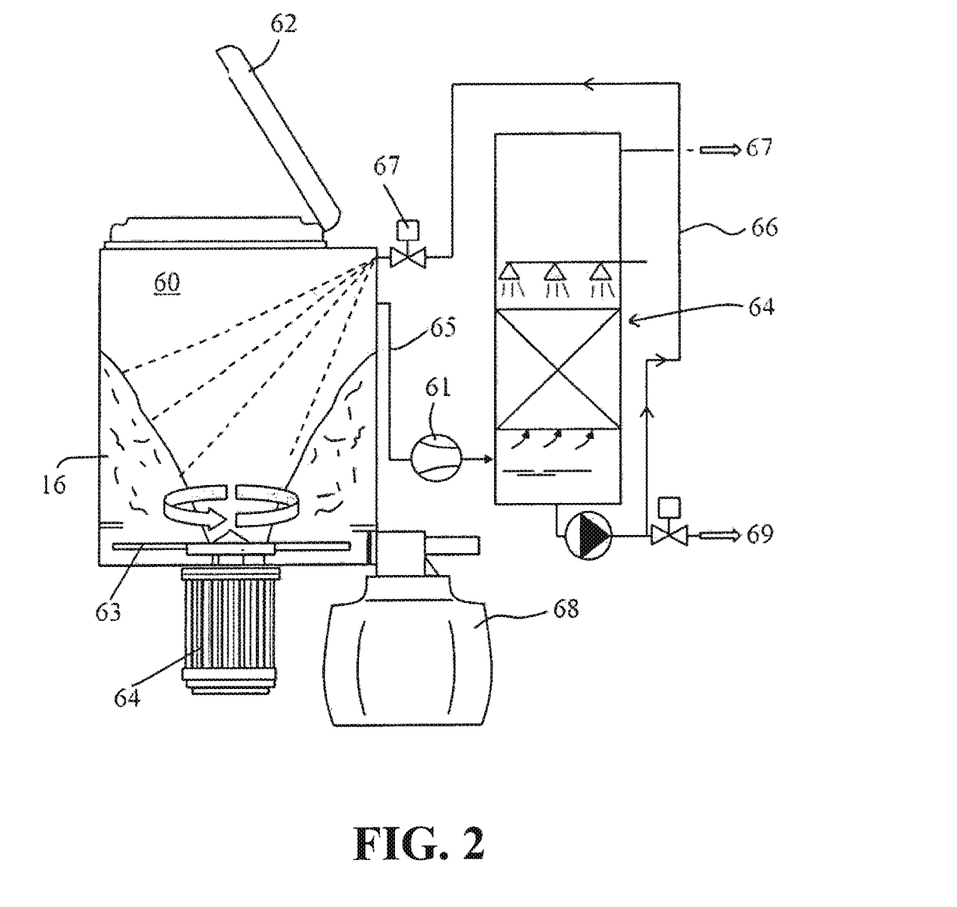
FIG. 2 is a schematic view of the converter.

A schematic illustration of this device is shown in FIG. 2.

With reference to this figure, the converter comprises a working and sterilization chamber 60, provided with a top opening for loading of the solid fraction 16. The opening is closed by a sealed cover 62, so as to enable vacuum conditions to be obtained inside the chamber 60 by a vacuum pump 61 connected to the chamber 60 by a duct 65. A fixed blade rotor 63 operated by a motor 64 is mounted in the lower part of the chamber 60.

The friction generated by the rotor 63 on the solid fraction 16 produces heating of said solid fraction from room temperature to a temperature from 55 to 160° C. Establishing these temperature conditions in the presence of the aforesaid vacuum conditions causes an effective evaporation of the residual water present in the solid fraction, which is drawn through the duct 65 and sent to a condenser 64. Therefore, the dual advantage of drying of the solid fraction and of its sanitization, due to the temperature reached, is achieved. This latter can be adjusted by controlled evaporation of water present in the solid fraction or by introducing a suitable amount of water from the outside through a duct 66 provided with a valve 67. The water used can come from recycling the water evaporated from the solid fraction or from other process or mains water. Evaporation of the water inside the chamber 60 produces cooling adapted to keep the temperature in the desired range. The combined mechanical and thermal effects of this milling treatment under vacuum produce a sanitized and bio-stabilized and/or sterilized dry solid, discharged for example into sacks 68 or into a conveyer belt, not illustrated. The solid can be transformed into briquettes or logs 24 and used as solid recovered fuel (SRF), also designated internationally as RDF (Refuse Derived Fuel), without the need for further treatments and with the advantage that it can be stored and transported as an inert material.

The condensate at the bottom of the chamber 60 is discharged through the line 69.

The rotary mill of "converter" type allows the treatment of waste from any source and of any composition and simultaneous sterilization or sanitization, modification of the physical state, reduction in volume, dehydration and reduction in weight.

The peculiarity of this device is that the waste is heated mechanically from within due to the heat produced by the friction generated by breaking up of the waste, by means of the powerful rotary blade positioned on the bottom of the mill. This takes place without the use of pressure or steam, making the whole treatment process much safer.

Due to operation at vacuum pressure, the evaporation temperature decreases in the working and sterilizing chamber 60, allowing a final product with reduced weight and volume, completely dry and safe to be obtained in less than 30 minutes. Any vapors or fumes of organic substance released by the solid fraction are extracted from the chamber 60 and sent to the biodigestor through the duct 67, also contributing to the formation of biogas.

More in particular, the milling treatment of said step a) comprises a step a1) of grinding in which the temperature rises from room temperature to 70-100° C.; a step a2) of evaporation in which the temperature is kept in the range 70-100° C.; a step a3) of overheating, in which the temperature of the material rises up to a value from 140 to 160° C., and a step a4) of sterilization, in which the temperature is kept from 140 to 160° C. for a time of from 1 to 10 minutes by dosing water, the evaporation of which compensates the heat produced by the material by friction.

The mill converter requires only recycled water, which is then treated in the anaerobic digestion process.

This device allows a mechanical-heat treatment cycle to be carried out, comprising grinding of the waste, evaporation of the liquids present, overheating of the material up to a sterilization temperature, which is kept for the required time, for example 3 minutes, by continuous dosing of water, cooling and discharge of the dry material. In a particularly preferred way, the following steps are carried out:

a0) Loading of the material (duration 2 minutes);

a1) Grinding (approximate duration 5 minutes), in which the temperature reaches the evaporation temperature as a function of the vacuum from 70° C. to 100° C.;

a2) Evaporation (approximate duration 7 minutes), in which the temperature is kept stable at the evaporation temperature;

a3) Overheating (approximate duration 3 minutes), in which the temperature of the material rises to the maximum of 160° C., preferably up to 151° C.;

a4) Sterilization (duration 3 minutes). In this step the temperature of the material is kept, for example, at 151° C. for 3 minutes by dosing water controlled by an infrared thermometer. The water, coming into contact with the material, evaporates turning rapidly into steam. When the water turns into steam it is replaced immediately. During this step, dosing of the water is controlled so as to contrast the heat produced by the material by friction. This mechanical-thermal combination damages the enzymes and the proteins of the microorganisms and, consequently, causes their death and destruction of the spores.

a5) Cooling (approximate duration. 1 minute);

a6) Discharge (approximate duration 1 minute). In this step the material is discharged by centrifugal force through a servo-controlled drain valve positioned on the bottom of the treatment cell. Once the material has been completely discharged, the rotor stops.

The liquid or semi-liquid fraction 18, resulting from the initial step of extrusion pressing of the waste, which usually forms 80-90% by weight of the waste fed to the press, is fed to a homogenization tank 26 and if necessary, water is added, including the water from evaporation produced in the step of milling under vacuum 20 (converter) and water from the subsequent treatments of anaerobic digestion, as described below. These additions allow a liquid to be obtained that is easily pumpable and with a concentration that promotes the biological processes.

According to an optional embodiment of the process according to the invention, it is also possible to treat sludges coming from a water treatment and purification plant. In this embodiment the sludges 25 are fed to the homogenization tank 26. Preferably, the sludges contain from 1 to 10% by weight of dry substance, more preferably from 3 to 8% by weight. Preferably, the concentration of solid in the liquor present in the homogenization tank 18 is no greater than 15% by weight, more preferably is no greater than 12% by weight. Usually, the minimum concentration of solid is 8%.

Figure 3:
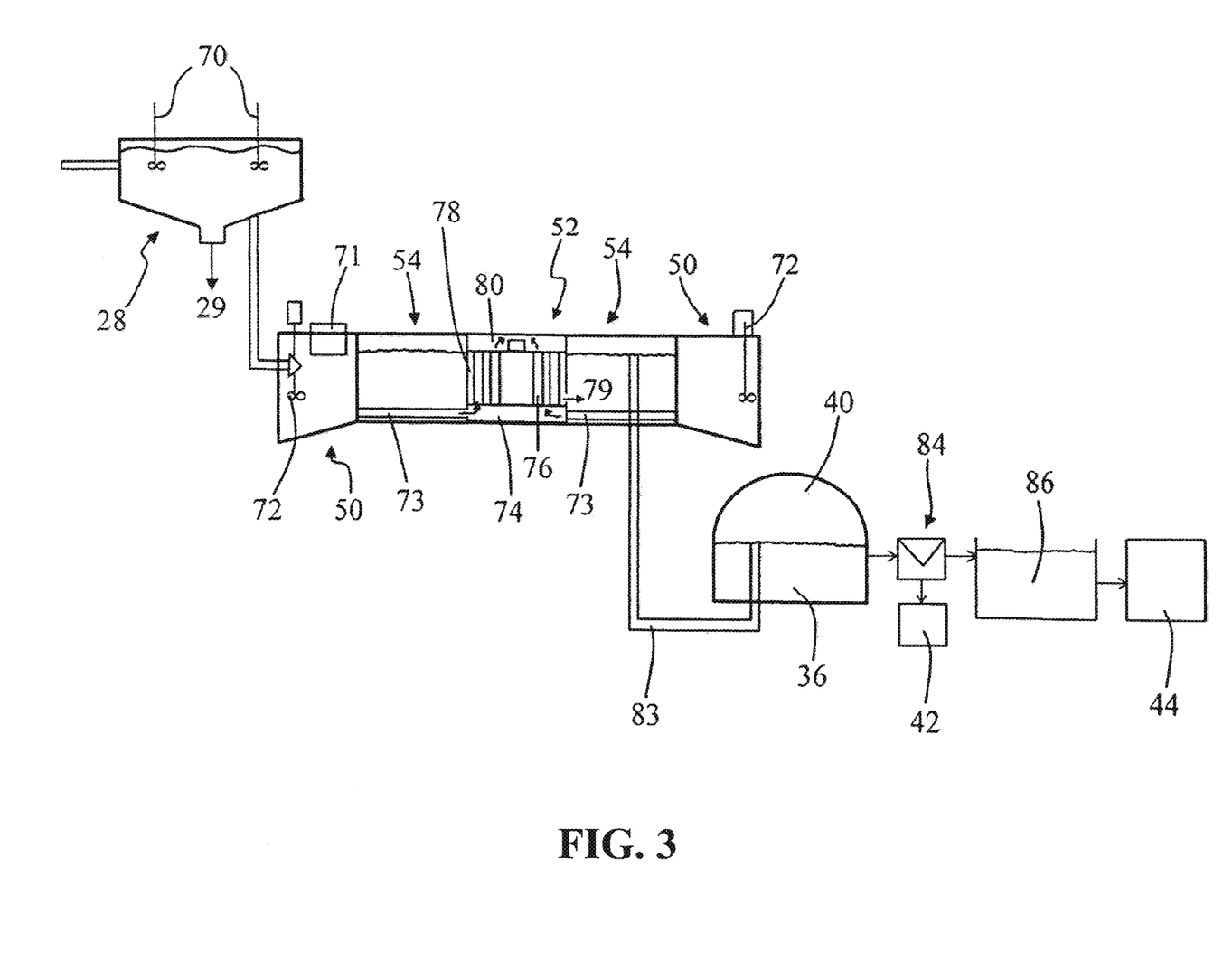
FIG. 3 is a schematic view of some operating units used in the process according to the invention.

With reference to FIGS. 1 and 3, the liquor, taken to the solid concentration desired, is stored temporarily in a buffer storage tank 28. The liquid is kept under gentle stirring by stirrers 70 inside the tank 28, which forms the reserve between the material arriving discontinuously and the continuous feed of the digestor in which the anaerobic digestion process will develop, and which will be adjusted as a function of the biogas pressure. Heavy solid residues, sands and the like are separated and sent, through the line 29, to the milling step 20. The tank 28 therefore has the function of compensating the feed, between the waste arriving and the biogas demand, for example, of a cogenerator associated with the waste treatment plant.

The liquid material accumulated in the tank 28 is then subjected to a treatment of anaerobic digestion in three subsequent steps.

In the first step 30 mesophilic fermentation is carried out at a temperature from 35 to 45° C., by the use of appropriate strains of mesophilic bacteria, as known in the art. Preferably, the mesophilic bacteria act at a temperature of 37° C. During fermentation biogas is produced naturally, and is stored in a gas holder 40.

The material that was subjected to the first treatment of mesophilic anaerobic digestion is then sent to a second step 32 at a temperature from 65 to 75° C., in which a pasteurization treatment is carried out, during which many potentially pathogenic microorganisms are destroyed or inactivated as a result of the heat. The biogas still produced is stored in the gas holder 40.

The material coming from the pasteurization treatment 32 is then fed to a third step of thermophilic fermentation 34 at a temperature from 50 to 60° C., through the use of suitable strains of thermophilic bacteria, as known in the art. Preferably, the thermophilic bacteria act at a temperature of 55° C. This treatment of anaerobic digestion produces a further amount of biogas, which is stored in the gas generator 40, and a digestate that is stored in a tank 36.

It was surprisingly found that the combination of the three treatments at the different temperature ranges indicated, with the geometrical arrangement of the process tanks described below, allows the production of biogas from the organic biomass to be maximized and a sanitized digestate, comprising a solid component dispersed in water, to be obtained, recovering the thermal energy used in pasteurization.

According to the invention, the aforesaid treatment of anaerobic digestion of the liquor in three subsequent steps is carried out in a series of concentric tanks.

With reference to FIG. 3, the mesophilic fermentation treatment 30 is carried out in a ring-shaped external tank 50, equipped with a tangential stirring system that allows all the material to remain constantly in the same tank. The stirring system comprises surface stirrers 71 and lower stirrers 72.

The material that has been subjected to the mesophilic fermentation treatment is then sent to the pasteurization treatment 32, which is carried out in an internal tank 52. The material is fed to the tank 52 through ducts 73 that pass through the intermediate tank 54.

Figure 4:
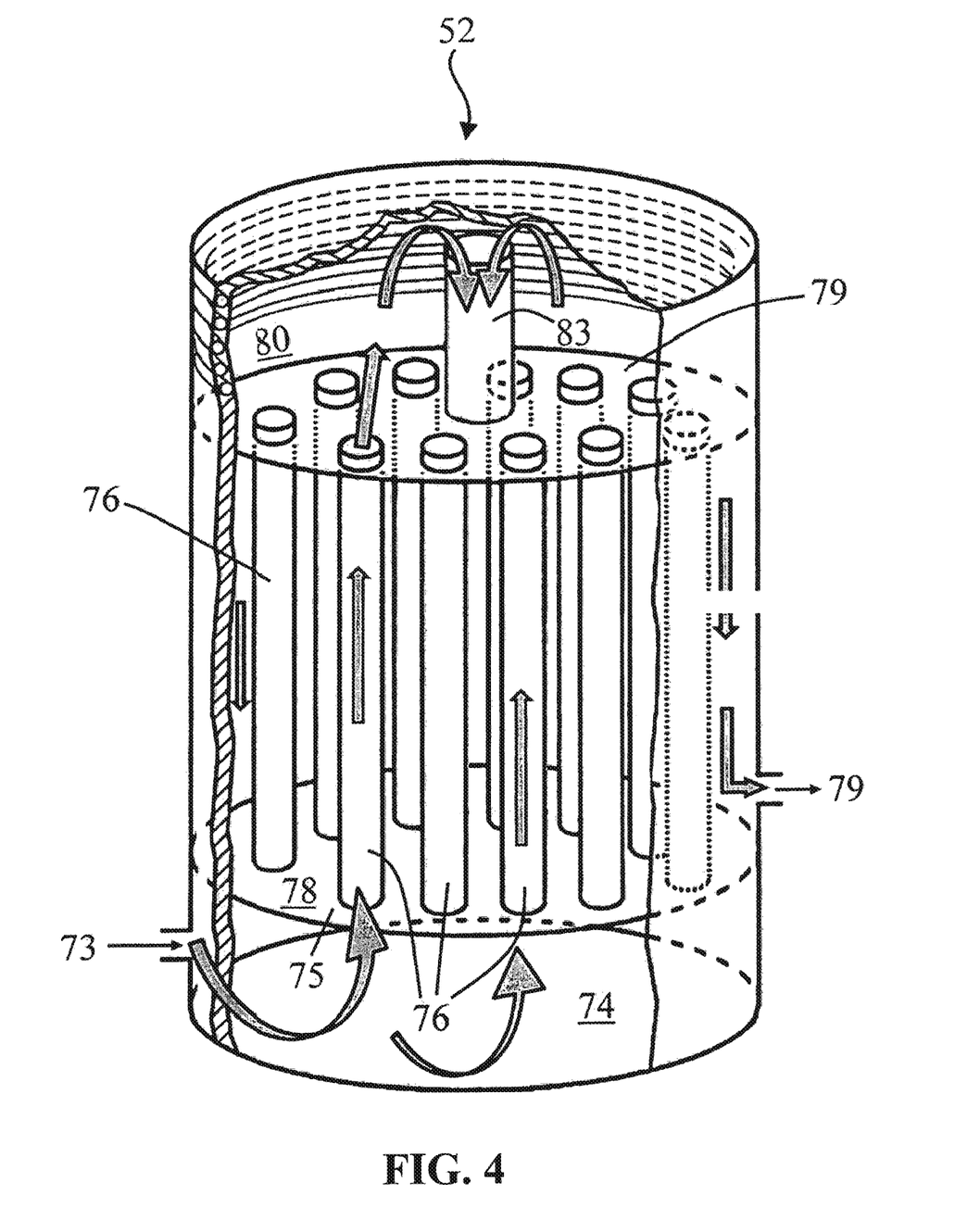
FIG. 4 is a partially sectional schematic perspective view of the internal tank of the anaerobic digestor according to the invention.

The pasteurization treatment 32 is carried out in an internal tank 52, composed of three separate chambers, as shown in detail in FIG. 4. With reference to FIGS. 3 and 4, the internal tank 52 comprises:
a) a first inlet chamber 74, for distribution of the inflowing liquid, coming through the ducts 73 from the mesophilic step 30 carried out in the tank 50, at around 40° C. The chamber 74 is provided with a perforated slab in which pipes 76 for the upward flow of the liquid are inserted;
b) a second intermediate chamber 78 of thermal exchange, closed at the top by a slab 79 provided with a central hole for the downward flow of the liquid and which is not in communication with the first chamber 74. The intermediate chamber 78 is suitably sized to maximize thermal exchange of the liquid that flows down at a temperature from 70-90° C. from the center of the third upper pasteurization tank 80. The liquid coming from the upper chamber flows down in countercurrent in the zone outside the pipes 76;
c) a third chamber 80, or proper pasteurization chamber, which is in communication with the first chamber 74 and with the second chamber 78. The liquid coming from the inlet chamber 74 inside the pipes 76 reaches the chamber 80 after having passed through the intermediate thermal exchange chamber 78, increasing its temperature to around 65-75° C. before entering the pasteurization zone, where it remains for at least 2 hours. The chamber 80 is equipped with a heating jacket, for example consisting of a coil 82 in which a heating fluid circulates, adapted to increase the temperature of the liquid to 65-90° C. Mounted on the central hole of the slab 79, which forms the base of the chamber 80, is an exit pipe 83 that extends in height close to the upper wall of the chamber 80. The liquid then exits into this pipe from the pasteurization chamber 80, through the pipe 83 and into the intermediate chamber 78 indicated in point b), touching the outer surface of the pipes 76 and transfers the heat in countercurrent to the liquid coming from the lower chamber 74. The liquid then exits from the internal tank 52 through the line 79 and is fed to the intermediate tank 54 where the thermophilic fermentation step is carried out. The decrease in temperature carried out in the intermediate chamber 78 lowers the temperature to the value required for thermophilic fermentation. i.e. from 50 to 60° C.

The amount of heat administered through the coil 82 of the chamber 80 and the related heights $h_1$ and $h_2$ of the chambers 78 and 80 are determined so as to achieve the temperatures desired and optimize thermal exchange.

Carrying out the three steps of anaerobic digestion in the three concentric tanks, preferably circular, as described, and producing the internal tank 52 with the three superimposed chambers 74, 78 and 80, with the related liquid flow paths, allows a reduction in energy consumption and avoids waste. In fact, the tank 52 for the pasteurization step, which operates at a higher temperature, is the innermost of the three tanks, while the tank 54, which operates at an intermediate temperature range, is in intermediate position, and the tank 50, which operates at the lowest temperature range, is positioned externally and is the largest. This arrangement of the tanks reduces heat loss and is adapted to help to keep the temperatures required for each single operation step, thereby improving the efficiency of the process. Also producing the internal tank 52 with the pasteurization chamber 80 positioned at the top and with a heating jacket as the only heating device of the whole anaerobic digestion process contributes to reducing energy consumption and to the efficiency of the process.

The tanks are provided with a surface stirring system to prevent the formation of scale, consisting of stirrers adjustable in height and direction. They are also provided with a conical base to facilitate separation of the decanted solid residues.

The digestate coming from the third step of thermophilic fermentation, sanitized with the process described is stored, through a duct 83, in the unheated storage tank 36, which cools the material, and which is provided with a slow stirring system and with a gas holder for compensation. The digestate is then pumped by a centrifuge 84 that separates a solid fraction 42 and a liquid fraction 86. The solid digestate 42 is sent to a container and subsequently transported by road to external composting plants.

The liquid fraction 46 can be in part recycled as is to the head of the plant and in part sent to an evaporation treatment under vacuum 44, to obtain a distillate 46 (around 80% of the material fed), which is in turn used as dilution water 48 for the homogenization tank 26 of the liquor 18, and in part destined for other uses (FIG. 1).

The evaporation treatment under vacuum 44 of the liquid fraction of the digestate also produces a dry sanitized compost 56, suitable to be used as fertilizer or improver in agriculture.

The biogas produced in the various steps of anaerobic digestion 30, 32, 34 is stored in the tank with gas holder 40, in which a slight overpressure forms, adjusted through pressure limiting devices to around 0.004 bar. The overpressure causes the gas to expand and enter a pressure switch accumulator made of plastic material (gas holder).

The process also includes a step 58 of purification and energy exploitation of the biogas produced.

This is obtained with the continuous contribution, through a small compressor, of a small amount of air suitably distributed by perforated pipes in the space in which the gas is stored, in a proportion of around 4% of air in volume. This amount of air produces a reaction of distributed desulfurization of the biogas, consisting of oxidation of the sulfurated substances with production of elemental sulfur, avoiding the formation of sulfurated hydrogen ($H_2S$), which could damage the subsequent biogas combustion devices. The steam present in the biogas is also separated by cooling and condensation, thereby avoiding damage to the biogas combustion devices.

In a preferred embodiment, the biogas is sent through a specific blower to a cogeneration unit 60 consisting of an internal combustion engine coupled to a synchronous alternator and completed by recovery of the cooling heat and of the flue gases. This system is adapted for the combined production of electric energy and heat.

The heat recovered from the cogeneration system is used in the heat exchangers of the plant to obtain the temperatures desired in the anaerobic fermentation steps described above.

Besides FORSU or RSU waste, the process according to the invention can also treat sludges from water purification plants and hospital waste, as described in the following examples.

EXAMPLE 1

Treatment of:
10000-30000 tons/year of FORSU or equivalent.

5000-20000 tons/year of liquid sludge from water treatment plants having from 3 to 8% of solid substance.
200-1000 tons/year of hospital waste.

Treatment of the aforesaid waste with the process according to the invention enabled a power plant with a power of 600-1500 kW to be supplied with the biogas produced for at least 8500 hours/year, with an electrical efficiency at full load of 42% and a thermal efficiency at full load of 40%. Around 70% of the electric energy produced was transferred to the electricity network and the co-generation system produced all the heat required for the process.

The process also produced 4000 tons/year of SRF and around 8000 tons/year of compost. Moreover, around 30000 tons/year of distilled water, in part re-used in the process, were produced. No pollutants or further waste products were produced.

EXAMPLE 2

Treatment of:
40000-80000 tons/year of FORSU or equivalent.
10000-40000 tons/year of liquid sludge from water treatment plants having from 3 to 8% of solid substance.
500-2000 tons/year of hospital waste.

Treatment of the aforesaid waste with the process according to the invention enabled a power plant with a power of 2-4 MW to be supplied with the biogas produced for at least 8500 hours/year. Around 30% of the electric energy produced was transferred to the electricity network and the co-generation system produced all the heat required for the process, also using part of the solid fuel produced.

The process also produced 8000 tons/year of SRF and around 12000 tons/year of compost. Moreover, around 50000 tons/year of distilled water, in part re-used in the process, were produced. No pollutants or further waste products were produced, but only heavy aggregates such as sand and residues of fine metals that can be used to process aggregates, or can be added to the solid fraction in the converter to increase the friction effect (max 5%).

It is evident from the examples provided that the process of the invention has a positive balance of the energy produced, which varies in percentage, according to the original material treated, from 80% to 50%. The only environmental impact of the process consists of the emissions from biogas combustion, which contain around 60% of methane, and of any combustion of SRF. Consequently, the process is pollution free if the plant is equipped with the normal scrubbing devices available on the market. Moreover, with the type of process used, material is not stored for more than one day, allowing daily washing of the receiving and pretreatment systems.

The invention claimed is:

1. A process for treating solid waste containing an organic fraction, comprising an initial step of extrusion pressing the waste with production of a solid fraction and a liquor, and further comprising the following steps:
   a) subjecting said solid fraction to a milling treatment at a pressure lower than the atmospheric pressure in a rotary mill that causes said solid fraction to heat from a room temperature to a sanitization temperature of from 55 to 160° C., said temperature being adjusted by controlled evaporation of water present in or introduced into said solid fraction, said milling treatment at a pressure lower than the atmospheric pressure producing a sanitized dry solid and water;
   b) combining said liquor to said water produced in said milling treatment of said step a), and subjecting it to a treatment of anaerobic digestion in three subsequent steps, comprising a first step of mesophilic fermentation at a temperature from 35 to 45° C., a second step at a temperature from 65 to 90° C., in which a pasteurization treatment is carried out, and a third step of thermophilic fermentation at a temperature from 50 to 60° C., said treatment of anaerobic digestion producing biogas and a digestate comprising a solid component dispersed in water;
   c) subjecting said digestate to an evaporation treatment of said water under vacuum in one or more steps, thereby producing a concentrated compost and steam which is condensed with formation of water which is in part used in other steps of the process and in part made available to be reused in the civil or agricultural or industrial field;
wherein said sanitized dry solid produced in said step a) and said biogas produced in said step b) are a fuel to produce thermal and electric energy, and said compost produced in said step c) is a fertilizer or improver in agriculture or is added to said solid fraction in said step a).

2. The process according to claim 1, wherein said milling treatment in said step a) is carried out at a pressure of from 0.03 to 0.08 MPa.

3. The process according to claim 1, wherein said milling treatment of said step a) comprises a step a1) of grinding in which the temperature rises from room temperature to 70-100° C.; a step a2) of evaporation in which the temperature is kept in the range 70-100° C.; a step a3) of overheating, in which the temperature of the material rises up to a value from 140 to 160° C., and a step a4) of sterilization, in which the temperature is kept from 140 to 160° C. for a time of from 1 to 10 minutes by dosing water, the evaporation of which compensates the heat produced by the material by friction.

4. The process according to claim 1, wherein said treatment of anaerobic digestion of the liquor in three subsequent steps is carried out in a series of concentric tanks, wherein the mesophilic fermentation treatment is carried out in the external tank, the pasteurization treatment is carried out in an internal tank, and the thermophilic fermentation treatment is carried out in an intermediate tank.

5. The process according to claim 4, wherein said internal tank comprises three separate chambers comprising an inlet chamber in which is fed the liquid coming from the mesophilic fermentation step at a temperature from 35 to 45° C., a pasteurization chamber where the liquid is heated to a temperature from 65 to 90° C. and where a pasteurization treatment is carried out, and a thermal exchange chamber, where the liquid coming from the pasteurization chamber releases heat whereby its temperature decreases to the temperature from 50 to 60° C. of the thermophilic fermentation step to which it is fed at the exit of said thermal exchange chamber, said treatment of anaerobic digestion producing said biogas and said digestate comprising a solid component dispersed in water.

6. A plant for treating solid waste containing an organic fraction, comprising an extrusion press for waste to produce a solid fraction and a liquor, a rotary mill to mill and heat said solid fraction, and a digestor for the anaerobic fermentation of said liquor, wherein said digestor comprises three concentric tanks consisting of an external tank for a treatment of mesophilic fermentation, an internal tank for a pasteurization treatment, and an intermediate tank for a treatment of thermophilic fermentation.

7. The plant according to claim 6, wherein said internal tank comprises three separate chambers, comprising:
  a) a first inlet chamber in which the liquid coming from the mesophilic step is distributed;
  b) a second intermediate chamber of thermal exchange, which is not in communication with said first chamber;
  c) a third chamber, of pasteurization, which is in communication with said first chamber and said second chamber, and which is adapted to receive the liquid coming from said first chamber through a series of pipes that extend into said second chamber hydraulically sealed from said second chamber, and to discharge said liquid in said second chamber through an exit pipe, said pasteurization chamber being equipped with a heating jacket;

and wherein said second chamber is equipped with a line to discharge the liquid from said internal tank into said intermediate tank for thermophilic fermentation.

* * * * *